United States Patent
Holzhacker et al.

(10) Patent No.: US 11,412,946 B2
(45) Date of Patent: Aug. 16, 2022

(54) ELECTRICAL IMPEDANCE TOMOGRAPHY DEVICE AND SYSTEM HAVING A MULTI-DIMENSIONAL ELECTRODE ARRANGEMENT

(71) Applicant: Timpel Medical B.V., Eindhoven (NL)

(72) Inventors: Rafael Holzhacker, São Paulo (BR); Elder Vieira Costa, São Paulo (BR)

(73) Assignee: Timpel Medical B.V., Eindhoven (NL)

( * ) Notice: Subject to any disclaimer, the term of this patent is extended or adjusted under 35 U.S.C. 154(b) by 1175 days.

(21) Appl. No.: 15/812,925

(22) Filed: Nov. 14, 2017

(65) Prior Publication Data
US 2019/0142299 A1    May 16, 2019

(51) Int. Cl.
*A61B 5/0536* (2021.01)
*A61B 5/00* (2006.01)

(52) U.S. Cl.
CPC .......... *A61B 5/0536* (2013.01); *A61B 5/0033* (2013.01); *A61B 5/6823* (2013.01); *A61B 5/6831* (2013.01); *A61B 5/748* (2013.01); *A61B 5/7435* (2013.01); *A61B 2562/0209* (2013.01); *A61B 2562/043* (2013.01); *A61B 2562/046* (2013.01); *A61B 2576/00* (2013.01)

(58) Field of Classification Search
CPC ... A61B 5/0536; A61B 5/0033; A61B 5/6823; A61B 5/6831; A61B 5/7435; A61B 5/748; A61B 2562/0209; A61B 2562/043; A61B 2562/046; A61B 2576/00
See application file for complete search history.

(56) References Cited

U.S. PATENT DOCUMENTS

| | | |
|---|---|---|
| 4,617,939 A | 10/1986 | Brown et al. |
| 4,920,490 A | 4/1990 | Isaacson |
| 5,272,624 A | 12/1993 | Gisser et al. |
| 5,284,142 A | 2/1994 | Goble et al. |
| 5,311,878 A | 5/1994 | Brown et al. |
| 5,351,697 A | 10/1994 | Cheney et al. |
| 5,381,333 A | 1/1995 | Isaacson et al. |

(Continued)

FOREIGN PATENT DOCUMENTS

| | | |
|---|---|---|
| BR | 0306103 A | 8/2005 |
| CN | 102499678 A | 6/2012 |

(Continued)

OTHER PUBLICATIONS

Kim, Minseo et al., "Wearable 3D Lung Ventilation Monitoring System with Multi Frequency Electrical Impedance Tomography" (Year: 2017).*

(Continued)

*Primary Examiner* — Eun Hwa Kim
*Assistant Examiner* — Adam Z Minchella
(74) *Attorney, Agent, or Firm* — TraskBritt

(57) ABSTRACT

Electrical impedance tomography devices and systems having a multi-dimensional electrode arrangement are disclosed including a related method for operating the devices and systems. The reconstructed images may correspond to the planes of the multi-dimensional electrode arrangements as well as one or more images corresponding to a region outside of the electrode planes. Such reconstruction may be performed by application of a finite element mesh having multiple layers defined for the different regions for generating the images.

20 Claims, 6 Drawing Sheets

(56) References Cited

U.S. PATENT DOCUMENTS

| | | | |
|---|---|---|---|
| 5,390,110 | A | 2/1995 | Cheney et al. |
| 5,544,662 | A | 8/1996 | Saulnier et al. |
| 5,588,429 | A | 12/1996 | Isaacson et al. |
| 5,626,146 | A | 5/1997 | Barber et al. |
| 5,807,251 | A | 9/1998 | Wang et al. |
| 5,919,142 | A | 7/1999 | Boone et al. |
| 6,014,583 | A | 1/2000 | Nakagawara et al. |
| 6,075,309 | A | 6/2000 | Wu |
| 6,387,671 | B1 | 5/2002 | Rubinsky et al. |
| 7,116,157 | B2 | 10/2006 | Ross et al. |
| 8,614,707 | B2 | 12/2013 | Warsito et al. |
| 9,639,928 | B2 | 5/2017 | Holzhacker |
| 2006/0116599 | A1 | 6/2006 | Davis |
| 2008/0319505 | A1 | 12/2008 | Boyden et al. |
| 2009/0234244 | A1* | 9/2009 | Tanaka ............... A61B 5/0536 600/547 |
| 2010/0010369 | A1* | 1/2010 | Pomfrett ............ A61B 5/0536 600/554 |
| 2010/0022904 | A1 | 1/2010 | Centen |
| 2010/0198101 | A1* | 8/2010 | Song ................... A61B 5/0871 600/547 |
| 2010/0210958 | A1 | 8/2010 | Manwaring et al. |
| 2010/0290675 | A1* | 11/2010 | Wexler ................. A61B 5/416 382/109 |
| 2011/0208028 | A1 | 8/2011 | Rossi |
| 2012/0035459 | A1 | 2/2012 | Revishvili et al. |
| 2012/0098549 | A1 | 4/2012 | Wang et al. |
| 2013/0002264 | A1 | 1/2013 | Garber |
| 2013/0190577 | A1 | 7/2013 | Brunner et al. |
| 2014/0371833 | A1 | 12/2014 | Ghosh et al. |
| 2015/0157865 | A1 | 6/2015 | Gillberg et al. |
| 2015/0342497 | A1 | 12/2015 | Maktura et al. |
| 2016/0302690 | A1* | 10/2016 | Nebuya ............... A61B 5/0536 |
| 2016/0341684 | A1* | 11/2016 | Choi ................... A61B 5/0538 |
| 2017/0172451 | A1* | 6/2017 | Boverman ............ G06T 11/003 |

FOREIGN PATENT DOCUMENTS

| | | |
|---|---|---|
| GB | 2216662 A | 2/1988 |
| WO | 2012037946 A1 | 3/2012 |
| WO | 2013110207 A1 | 8/2013 |
| WO | 2015025113 A1 | 2/2015 |
| WO | WO-2015025113 A1 * | 2/2015 ............ A61B 5/004 |
| WO | 2015048917 A1 | 4/2015 |
| WO | 2015083958 A1 | 6/2015 |
| WO | 2015089008 A1 | 6/2015 |

OTHER PUBLICATIONS

Cano, "Annex C. Instrumentation for Electrical Bioimpedance Measurements", In: "PhD Dissertation: Contributions to the Measurement of Electrical Impedance For Living Tissue Ischemia Injury Monitoring", (Feb. 1, 2005), pp. 187-217.

Holder, David S., "Electrical Impedance Tomography—Methods, History and Applications," 2005, Chapter 2 and Appendix B, Series in Medical Physics and Biomedical Engineering, Institute of Physics Publishing Ltd., Bristol and Philadelphia, 464 pages.

Koukourlis, et al., "Differential Synchronous Demodulation for Small-Signal Amplitude Estimation", IEEE Transactions on Instrumentation and Measurement, vol. 42, No. 5, (Oct. 1, 1993), pp. 926-931.

Wi, et al., "Expandable Multi-frequency EIT System for Clinical Applications," Progress In Electromagnetics Research Symposium Proceedings, Mar. 27-30, 2012, pp. 49-52, Kuala Lumpur, Malaysia.

Minseo et al., "Wearable 3D lung ventilation monitoring system with multi frequency electrical impedance tomography", 2017 IEEE Biomedical Circuits and Systems Conference (BIOCAS), Oct. 20, 2017, pp. 1-4.

Minseo et al., "A 1.4-m $\Omega$—Sensitivity 94-dB Dynamic-Range Electrical Impedance Tomography SoC and 48-Channel Hub-Soc for 2-D Lung Ventilation Monitoring System", IEEE Journal of Solid-State Circuits, vol. 52, No. 11, Oct. 3, 2017, pp. 2829-2842.

International Written Opinion from International Application No. PCT/IB2018/057611, dated Dec. 19, 2018, 8 pages.

International Search Report from International Application No. PCT/IB2018/057611, dated Dec. 19, 2018, 4 pages.

Bayford et al., "Development of a neonate lung reconstruction algorithm using a wavelet AMG and estimated boundary form", Physiological Measurement, vol. 29, No. 6, Jun. 1, 2008, pp. S125-S138.

\* cited by examiner

ELECTRICAL IMPEDANCE TOMOGRAPHY DEVICE AND SYSTEM HAVING A MULTI-DIMENSIONAL ELECTRODE ARRANGEMENT

TECHNICAL FIELD

The disclosure relates to electrical impedance tomography systems generally, and more specifically, to an electrical impedance tomography system having a multi-dimensional electrode arrangement generating imaging data outside the electrode planes.

BACKGROUND

Electrical impedance tomography (EIT) is an imaging technique involving the positioning electrodes via an electrode belt placed around a region of a patient's body (e.g., around the patient's chest for imaging of a lung), injecting electrical excitation signals through a pair of electrodes, and measuring the induced response signals detected by the other electrodes of the electrode belt. As a result, the EIT system may generate an image based on the voltage measurements indicating estimated impedance values. In contrast with other imaging techniques, EIT is non-invasive and does not have certain exposure risks that might limit the number and frequency of monitoring actions (e.g., as with techniques such as X-rays). As a result, EIT is suitable for continuously monitoring the condition of the patient, with particular application to monitoring the patient's lungs as the measurements may be used to determine respiratory and hemodynamic parameters of the patient and monitor a real-time two-dimensional image.

FIG. 1 is a schematic diagram of a portion of an EIT system 100 showing a plurality of electrodes 110 positioned around a region of interest (e.g., thorax) of a patient 105. The electrodes 110 of conventional EIT systems 100 are typically physically held in place by an electrode belt to ensure consistent spacing as well as a linear (one dimensional) alignment of the electrodes 110. The placement of the electrodes 110 is typically in a single plane 102 transverse to the cranial caudal axis 104 of the patient. Although the electrodes 110 are shown in FIG. 1 as being placed only partially around the patient 105, electrodes 110 may by placed around the entire patient 105 depending on the specific region of interest available or desired for measurement. The electrodes 110 may be coupled to a computing system (not shown) configured to control the operation of the electrodes 110 and perform reconstruction of the EIT image.

FIG. 2 is a schematic diagram showing a cross-section of the thorax of the patient 105 along the plane of the electrodes. A voltage may be applied to a pair of electrodes 110 (shown by the electrodes having a + and − symbol) to inject an excitation current into the patient between an electrode pair. As a result, voltages (e.g., $V_1, V_2, V_3 \ldots V_n$) may be detected by the other electrodes and measured by the EIT system 100. Current injection may be performed for a measurement cycle according to a circular pattern using different electrode pairs to generate the excitation current.

FIG. 3 is a schematic representation of a finite element mesh 300 utilized by the EIT system as a starting point for reconstruction of the EIT image 400 (FIG. 4). The finite element mesh 300 is a numerical simulation created to model the impedance of the patient's body for a region corresponding to the desired placement of the electrodes 110. The finite element mesh 300 may be stored in memory of the EIT device and utilized by the reconstruction algorithm to interpret the measurements and generate the image. Conventional EIT systems using electrodes 110 arranged linearly in a single plane 302 may also utilize a finite element mesh 300 having a thickness corresponding to approximately the region of the electrodes 110, and that is defined by the system as a single layer for reconstructing the image.

BRIEF SUMMARY

In some embodiments, an electrical impedance tomography system is disclosed. The electrical impedance tomography system comprises an electrode belt including electrodes arranged in at least two planes vertically spaced from each other, and a data acquisition system operably coupled with the electrode belt. The data acquisition system is configured to inject an excitation current into successive pairs of the electrodes, measure a voltage response utilizing pairs of the electrodes of the electrode belt, and reconstruct images from the measured voltages indicative of impedances for at least one region of interest outside of the planes of the electrodes.

In some embodiments, an electrical impedance tomography system comprises a data acquisition system including a memory device having a plurality of finite element meshes stored therein, and a processor operably coupled with the memory device and the electronic display. Each finite element mesh has a plurality of regions of interest for reconstructing an image along with a corresponding reconstruction matrix for use by the reconstruction algorithm. The processor is configured to receive voltage measurements from an electrode belt having electrodes in at least two planes, reconstruct images for the voltage measurements and the reconstruction matrix for the selected layers of the selected finite element mesh, and cause the reconstructed images to be displayed on an electronic display.

In some embodiments, a method of operating an electrical impedance tomography device is disclosed. The method comprises injecting an excitation current into successive pairs of electrodes in an electrode belt having electrodes arranged in multiple horizontal planes, measuring a voltage response utilizing pairs of the electrodes not being used for current injection, and reconstructing and displaying images from the measured voltages indicative of impedances for regions corresponding to the planes of the electrodes and for regions outside of the planes of the electrodes.

DETAILED DESCRIPTION

Figure 1:
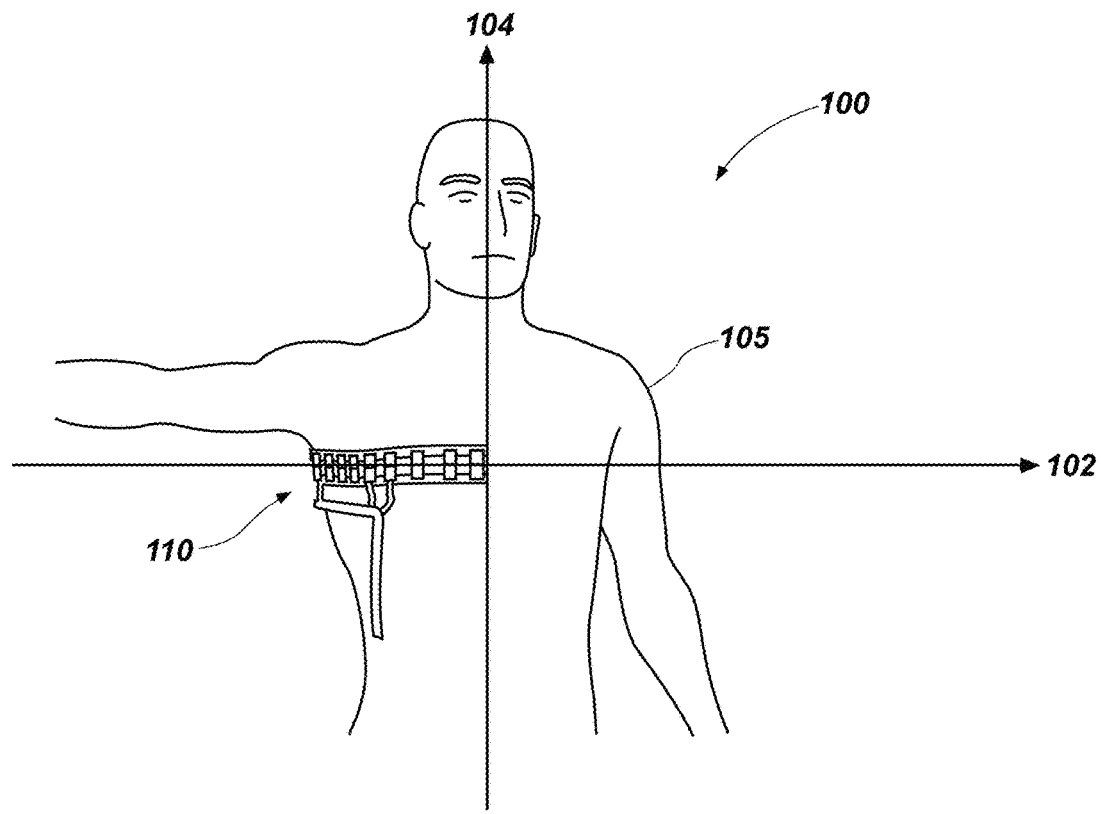
FIG. 1 is a schematic diagram of a portion of an EIT system showing a plurality of electrodes positioned around a region of interest of a patient.
Figure 2:
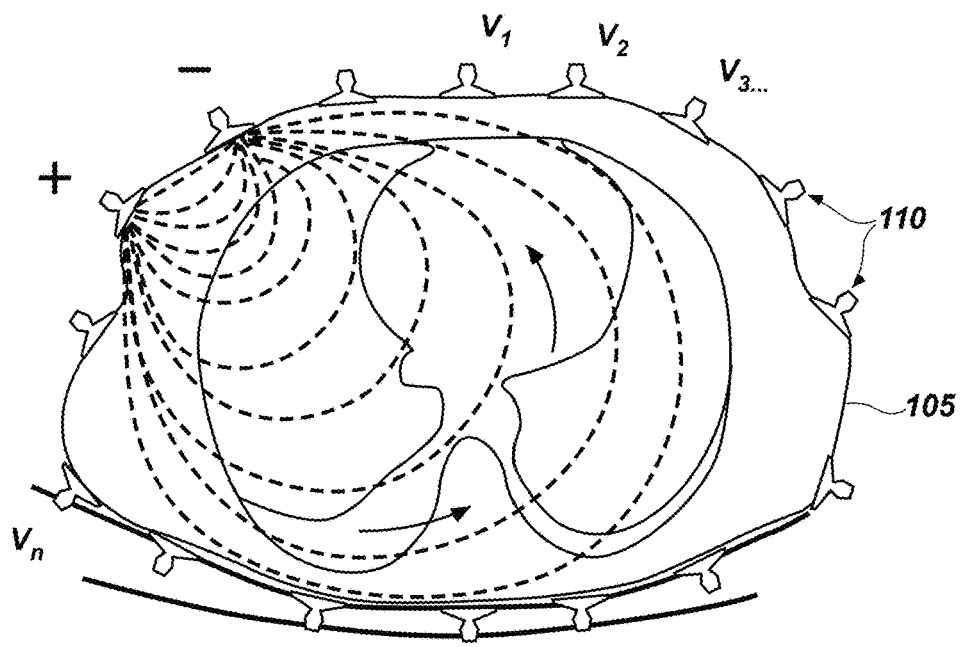
FIG. 2 is a schematic diagram showing a cross-section of the thorax of the patient along the plane of the electrodes.
Figure 3:
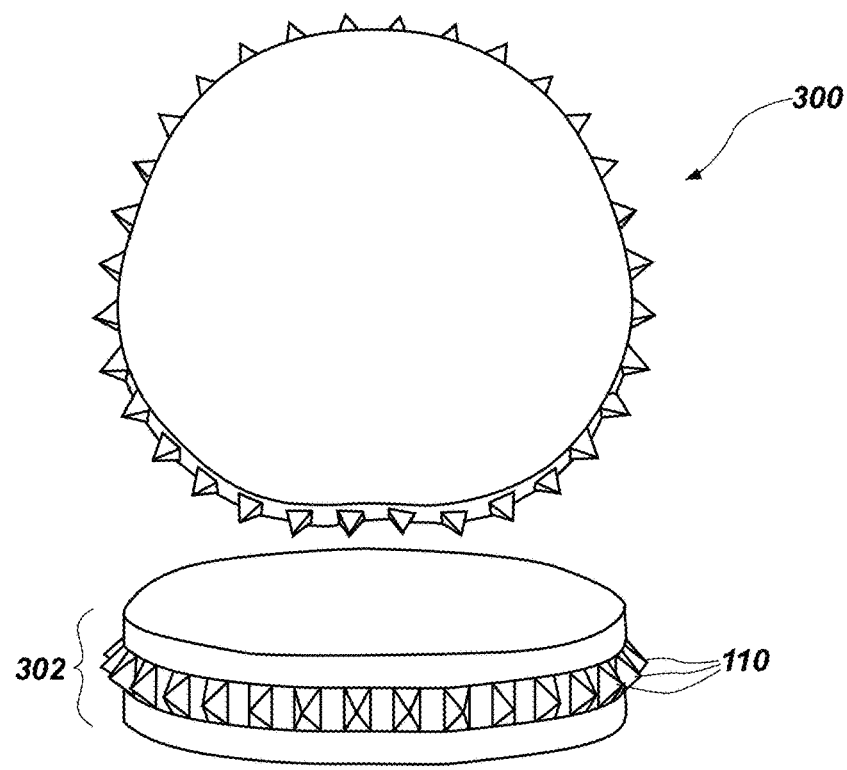
FIG. 3 is a schematic representation of a finite element mesh utilized by the EIT system as a starting point for reconstruction of the EIT image.
Figure 4:
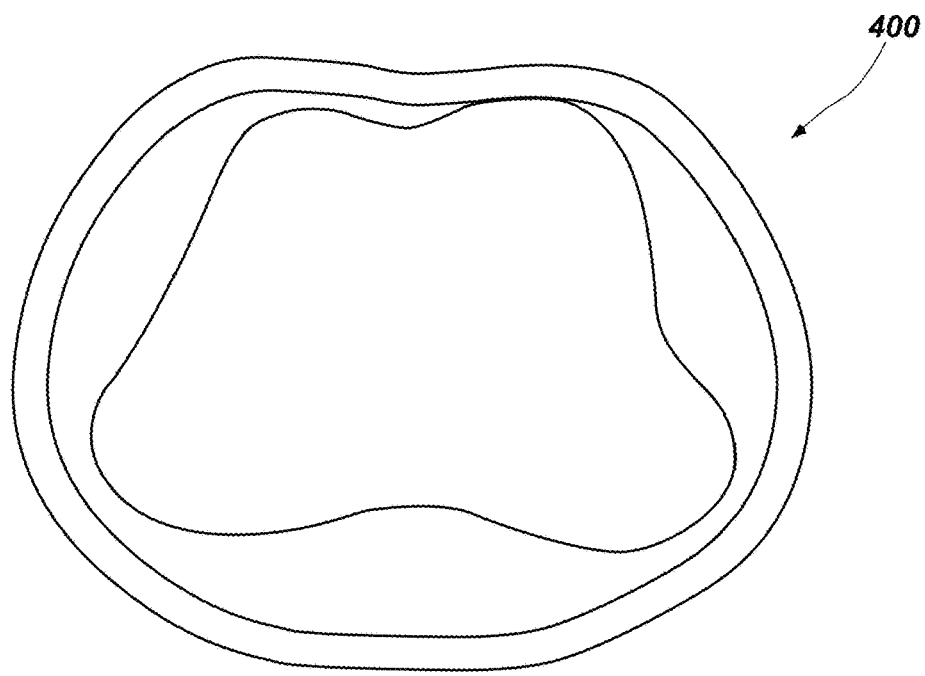
FIG. 4 is an example of an image reconstructed by a conventional EIT system.

In the following detailed description, reference is made to the accompanying drawings which form a part hereof, and in which is shown by way of illustration specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice the various features illustrated in the drawings may not be drawn to scale. The illustrations presented herein are not meant to be actual views of any particular apparatus (e.g., device, system, etc.) or method, but are merely representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus or all operations of a particular method.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the disclosure may be implemented on any number of data signals including a single data signal.

The various illustrative logical blocks, modules, and circuits described in connection with the embodiments disclosed herein may be implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A general-purpose processor may be considered a special-purpose processor while the general-purpose processor executes instructions (e.g., software code) stored on a computer-readable medium. A processor may also be implemented as a combination of computing devices, e.g., a combination of a DSP and a microprocessor, a plurality of microprocessors, one or more microprocessors in conjunction with a DSP core, or any other such configuration.

Also, it is noted that embodiments may be described in terms of a process that may be depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media include both computer storage media and communication media, including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

An electrode "plane" as used herein refers to electrodes that are at least substantially linearly placed along the longitudinal direction of the electrode belt—i.e., the direction of the belt that is transverse to the cranial caudal axis of the patient when applied to the chest of the patient. At times, the longitudinal direction may appear as the x-axis and be referred to as horizontal. The cranial caudal axis may also appear in the figures as the y-axis and be referred to as vertical. Terms such as horizontal/vertical or x-axis/y-axis are based on the orientation shown in the figures herein. References to "patient" or "body" may be applicable to humans or animals, as well to imaging applications of other objects.

When referring to an electrode pair, a dash (-) may be used to separate the electrodes numbers of the pair (i.e., 1-3, 2-4, 3-5, etc.) and does not mean a range of electrodes. In other words, electrodes (1-3) means electrode pair 1 and 3, and does not mean electrodes 1 through 3.

Figure 5:
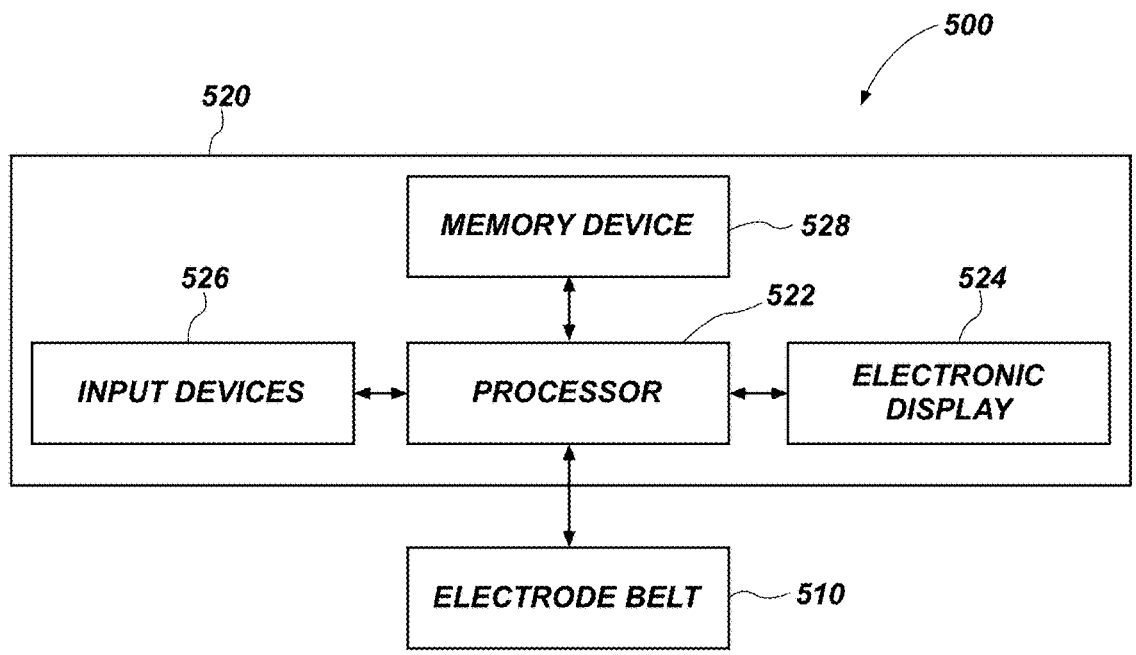
FIG. 5 is a schematic block diagram of an EIT system according to an embodiment of the disclosure.

FIG. 5 is a schematic block diagram of an EIT system 500 according to an embodiment of the disclosure. The EIT system 500 may include an electrode belt 510 operably coupled with a data processing system 520. The electrode belt 510 and the data processing system 520 may be coupled together via a wired connection (e.g., cables) and/or may have communication modules to communicate wirelessly with each other. The data processing system 520 may include a processor 522 operably coupled with an electronic display 524, input devices 526, and a memory device 528. The electronic display 524 may be constructed with the data processing system 520 into a singular form factor for an EIT device coupled with the electrode belt 510. In some embodiments, the electronic display 524 and the data processing system 520 may be separate units of the EIT device coupled with the electrode belt 510. In yet other embodiments, an EIT system 500 may be integrated within another host system configured to perform additional medical measurements and/or procedures, in which the electrode belt 510 may couple to a port of the host system already having its own input devices, memory devices, and electronic display. As such, the host system may have the EIT processing software installed therein. Such software may be built into the host system prior field use or updated after installation.

The processor 522 may coordinate the communication between the various devices as well as execute instructions stored in computer-readable media of the memory device 528 to direct current excitation, data acquisition, data analysis, and/or image reconstruction. As an example, the memory device 528 may include a library of finite element meshes as will be discussed further below that is used by the processor 522 to model the patient's body in the region of interest for performing image reconstruction. Input devices 526 may include devices such as a keyboard, touch screen interface, computer mouse, remote control, mobile devices, or other devices that are configured to receive information that may be used by the processor 522 to receive inputs from an operator of the EIT system 500. Thus, for a touch screen interface the electronic display 524 and the input devices 526 receiving user input may be integrated within the same device. The electronic display 524 may be configured to receive the data and output the EIT image reconstructed by the processor for the operator to view. Additional data (e.g., numeric data, graphs, trend information, and other information deemed useful for the operator) may also be generated by the processor 522 from the measured EIT data alone, or in combination with other non-EIT data according to other equipment coupled thereto. Such additional data may be displayed on the electronic display 524.

The EIT system 500 may include components that are not shown in the figures, but may also be included to facilitate communication and/or current excitation with the electrode belt 510 as would be understood by one of ordinary skill in the art, such as including one or more analog to digital converter, signal treatment circuits, demodulation circuits, power sources, etc.

Figure 6:
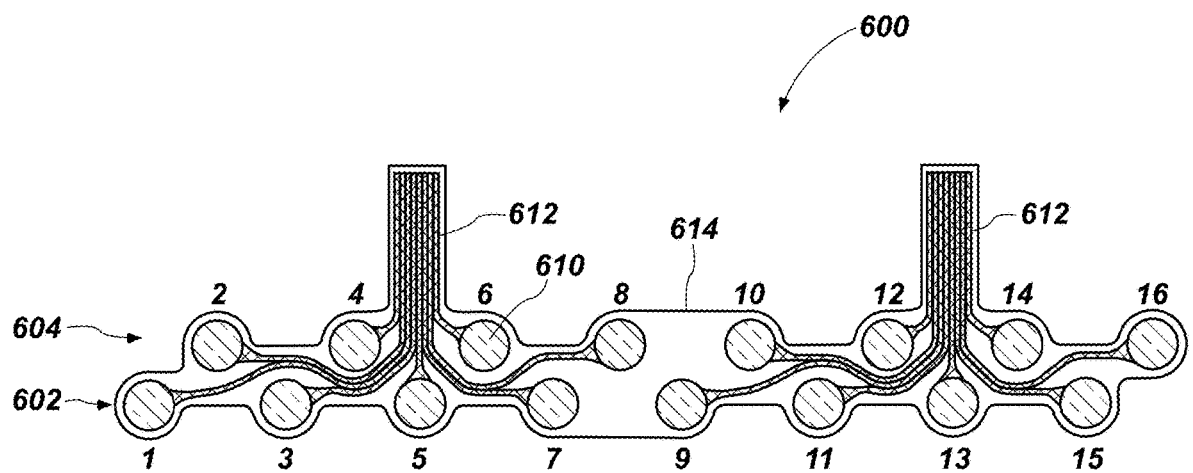
FIG. 6 is a schematic diagram of an electrode belt according to an embodiment of the disclosure.

FIG. 6 is a schematic diagram of an electrode belt 600 according to an embodiment of the disclosure. For example, the electrode belt 600 may be the electrode belt 510 of FIG. 5. The electrode belt 600 may include electrodes 610 coupled to cables 612 that are further coupled to a data acquisition system (FIG. 5). The electrodes 610 may be secured by a belt material 614 (e.g., fabric, gel, adhesive materials, etc.) that may be placed around the body of the patient. The electrode belt 600 may be placed around a portion of the body, or all of the body, depending on the desired or available region to be imaged. Electrodes 610 are also referred to individually by numbers 1-16 to correspond to a particular electrode (e.g., electrode 1=first electrode, electrode 2=second electrode . . . electrode 16=sixteenth electrode). Although 16 electrodes 610 are shown in FIG. 6, it is contemplated that electrode belts having a different number (e.g., 32) of electrodes may be utilized depending on the desired image resolution and/or size of the patient. One or more sets of cables 612 may also be used to couple the electrodes 610 with the data acquisition system.

As shown in FIG. 6, the electrodes 610 may be arranged in a first plane 602 and a second plane 604. Arranging the electrodes 610 into additional planes (e.g., more than two planes) is also contemplated. In some embodiments, the electrodes 610 of the first plane 602 may be horizontally offset from the electrodes 610 of the second plane 604. As a result, the electrodes 610 of the first plane 602 may be shifted horizontally relative to the electrodes 610 of the second plane 604 (e.g., in a zigzag pattern), such that electrodes 610 of one plane may be aligned vertically with the space between electrodes 610 of the other plane. In some embodiments, the electrodes 610 of adjacent planes may be substantially aligned along the respective horizontal planes relative to each other (e.g., in a stacked pattern). Each plane 602, 604 may include a number of electrodes 610. For example, in an embodiment having 16 electrodes, the first plane 602 may include 8 electrodes and the second plane 604 may include 8 electrodes. In an embodiment having 32 electrodes, the first plane 602 may include 16 electrodes and the second plane 604 may include 16 electrodes. Thus, each plane 602, 604 may have the same number of electrodes as each other. Embodiments may also include planes 602, 604 having a different number of electrodes 610. For example, in an embodiment having 16 electrodes, the first plane 602 may include 12 electrodes and the second plane 604 may include 4 electrodes (or some other combination, such as 4, 12; 6, 10; 10, 6; etc.). Embodiments having 32 electrodes may also include planes 602, 604 having different number of electrodes (e.g., 12, 20; 14, 18; 18, 14; 20, 12; etc.). In addition, different numbers and combinations of electrodes than 16 and 32 are also contemplated.

In operation, an excitation current may be injected into successive pairs of electrodes and the induced voltages in the other electrodes may be measured and a voltage vector for each measurement may be generated and analyzed for one or more measurement cycles around the region of interest. These voltage values may be indicative of impedance of the body, and the impedance measurements may be reconstructed to an image displayed by the EIT system. In some embodiments, the measurements of the induced signals in the measurement electrodes occur substantially simultaneously. Of course, the body does not have a uniform composition and phases of the measured signals may be offset by processor 522 when reconstructing the image. In some embodiments, the excitation current may be a high frequency AC signal (e.g., between 10 kHz and 2.5 MHz), the response to which may be measured by the measurement electrodes. In addition, in some embodiments low frequency signals may also be extracted from the measurements that are indicative of hemodynamic and breathing activities. For example, signals on the order of about 1 Hz to 4 Hz may be indicative of heartbeats and lower than 1 Hz may be indicative of breathing. Generally, approximately 20 to 100 measurement cycles per second (images per second) are generated. Other measurement cycles are also contemplated as supported by performance characteristics of the different components of the EIT system.

Various rotation patterns for utilizing the electrodes are contemplated as embodiments of the disclosure. In some embodiments, the rotation pattern for a measurement cycle may include injecting the excitation current with electrodes of the first plane 602 and then the electrodes of the second plane 604. Measurements with the other electrodes are merged to reconstruct and display the image on the EIT device. For example, a measurement cycle may include first utilizing electrodes (1-3; 3-5; 5-7; . . . etc.) of the first plane 602 to generate the excitation currents and then the electrodes (2-4; 4-6; 6-8; . . . etc.) of the second plane 604 to generate the excitation currents after all electrode pairs of the first plane 604 have been utilized. In each instance the non-current inducing electrodes measure the voltages to determine the impedances as discussed above. In another example, the electrode pairs may not be directly adjacent. For example, electrode pairs may be separated by one or more intervening electrodes, such as utilizing electrodes (1-5; 3-7; 5-9; . . . etc.) of the first plane 602 to generate the excitation current, and then electrodes (2-6; 4-8; 6-10; . . . etc.) to generate the excitation current. Such an embodiment may be referred to as "interleaved." Interleaved rotation patterns may skip one electrode (e.g., 1-5; 3-7; 5-9; . . . etc.) in its respective plane when generating the excitation current. Likewise, measurement electrodes may also skip one electrode. Interleaved rotation patterns may also skip additional electrodes (e.g., 1-7; 3-9; 5-11; . . . etc.) in its respective plane when generating the excitation current.

In some embodiments, the rotation pattern may include injecting the excitation current by alternating between electrodes of the first plane 602 and the electrodes of the second plane 604. Measurements with the non-current inducing electrodes are merged to reconstruct and display the image. For example, electrodes (1-3) of the first plane 602 may generate the excitation current, followed by electrodes (2-4) of the second plane 604, which may then be utilized to generate the excitation current. The measurement cycle may continue with electrodes (3-5; 4-6; 5-7; 6-8; . . . etc.) from each plane 602, 604 each taking a turn to generate the excitation current while the other electrodes are utilized to perform measurements until completing a measurement cycle around the region of interest. Such a rotation pattern may also employ an interleaved order of operation. For example, excitation may occur with electrodes (1-5; 2-6; 3-7; 4-8; . . . etc.) or electrodes (1-7; 2-8; 3-9; 4-10; . . . etc.) depending on the number of intervening electrodes desired.

In some embodiments, the rotation pattern may include injecting the excitation current utilizing electrode pairs arranged diagonally in different planes 602, 604. For example, electrodes (1-2, 2-3, 3-4, etc.) may be utilized to generate the excitation current during the measurement cycle. Such a rotation pattern may also employ an interleaved order of operation. For example, excitation may occur with electrodes (1-4; 2-5; 3-6; 4-7; . . . etc.). In some embodiments, other non-sequential rotation patterns are also contemplated. For example, excitation may occur with non-sequential electrodes (1-4; 16-19; 17-20; 2-5; . . . ) etc.).

Figure 7:
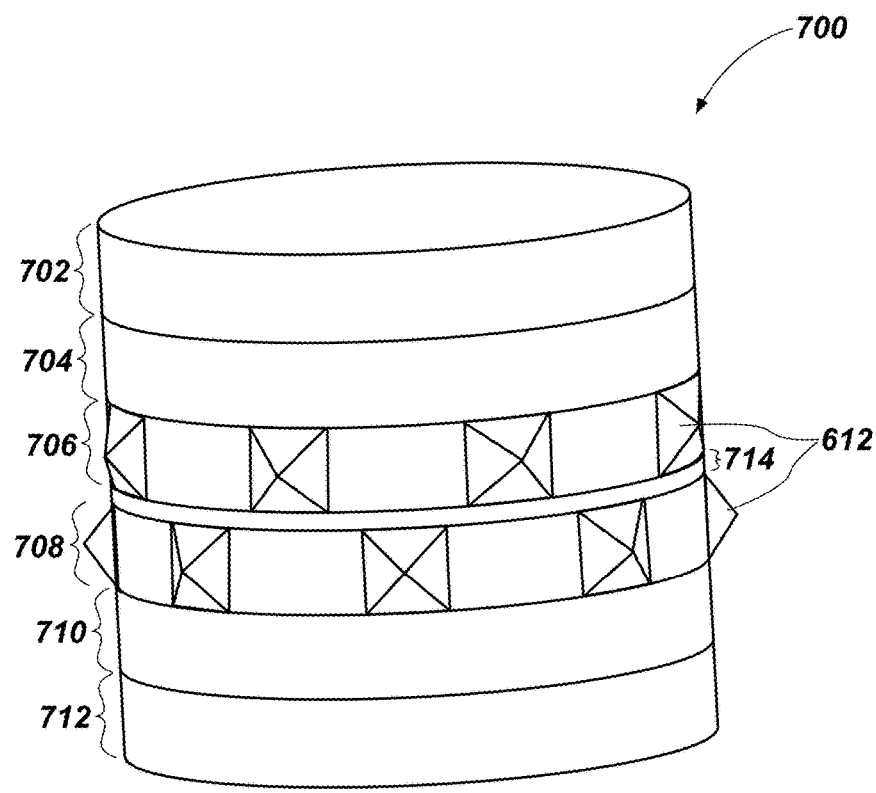
FIG. 7 is a schematic representation of a finite element mesh utilized by the processor when reconstructing the image from the voltage measurements according to an embodiment of the disclosure.

FIG. 7 is a perspective view of a schematic representation of a finite element mesh 700 utilized by the processor 522 when generating the reconstruction matrices used for reconstructing the image from the voltage measurements according to an embodiment of the disclosure. The finite element mesh 700 is a numerical simulation used to model the resistivity of the body whose electrical impedance image is to be reconstructed. The finite element mesh 700 is three-dimensional (3D) whereas the extracted image is two-dimensional (2D). The protruding elements represent the electrodes 610. As the patient's body may not exhibit a uniform resistivity, the body of the finite element mesh 700 also may not be modeled with a uniform resistivity matrix. The resistivity may vary throughout the finite element mesh 700 in each dimension of the matrix. When reconstructing the image, the voltage measurements from the different electrodes are applied to the reconstruction matrices generated from the resistivity values of the finite element mesh 700 to reduce error resulting from application to the resistivity matrix to determine the impedance values displayed by the reconstructed image.

The finite element mesh 700 may be logically divided into multiple regions of interest. For example, the finite element mesh 700 of FIG. 7 has been divided into 7 layers—the first and second layers 702, 704 may be regions above third and fourth layers 706, 708 (also referred to as the electrode layers). The fifth and sixth layers 710, 712 may be below the electrode layers 706, 708. A seventh layer 714 may also be defined as the thin region between the electrode layers 706, 708. Other numbers of layers are also contemplated, including additional layers subdividing the layers 702, 704, 710, 712 above or below the electrode layers 706, 708. In addition, depending on the spacing of the electrodes, some layers may be defined between the electrode layers 706, 708. The layers may have uniform thicknesses or different thicknesses in the various embodiments. In some cases, defining a layer to be thinner may increase the accuracy of the reconstructed image for that layer.

It should be noted that the finite element mesh 700 of FIG. 7 is a generic cylindrical shape; however, different shapes are also contemplated to more accurately account for different shapes and body types of the patient. The memory of the EIT device may store a library of different finite element meshes from which the equipment operator can select to be approximate the body of the patient.

Prior to reconstruction, the finite element mesh 700 may be used to generate one or more reconstruction matrices. A different reconstruction matrix may be generated for each layer defined in the finite element mesh 700. For example, a first reconstruction matrix may be generated for the first layer 702, a second reconstruction matrix may be generated for the second layer 704, a third reconstruction matrix may be generated for the third layer 706, a fourth reconstruction matrix may be generated for the fourth layer 708, a fifth reconstruction matrix may be generated for the fifth layer 710, a sixth reconstruction matrix may be generated for the sixth layer 712, and a seventh reconstruction matrix may be generated for the seventh layer 714 and/or any other number of reconstruction matrices depending on the number of defined layers. The impedances of all layers of the finite element mesh 700 may be weighted by each respective reconstruction matrix to contribute to the reconstructed image for a given layer as the current does not flow in a straight line throughout the body. The contribution of the impedance may be stronger closer to the electrodes, and weaker for regions more remote from the electrodes.

During reconstruction, the voltage vectors generated by the measurement electrodes are applied to one or more reconstruction matrix. The EIT device may be configured to generate a reconstructed image for each layer 702-714 defined by the finite element mesh 700. In other embodiments, the EIT device may be configured to generate a reconstructed image for a subset of the layers 702-714 as selected by the operator.

Figure 8:
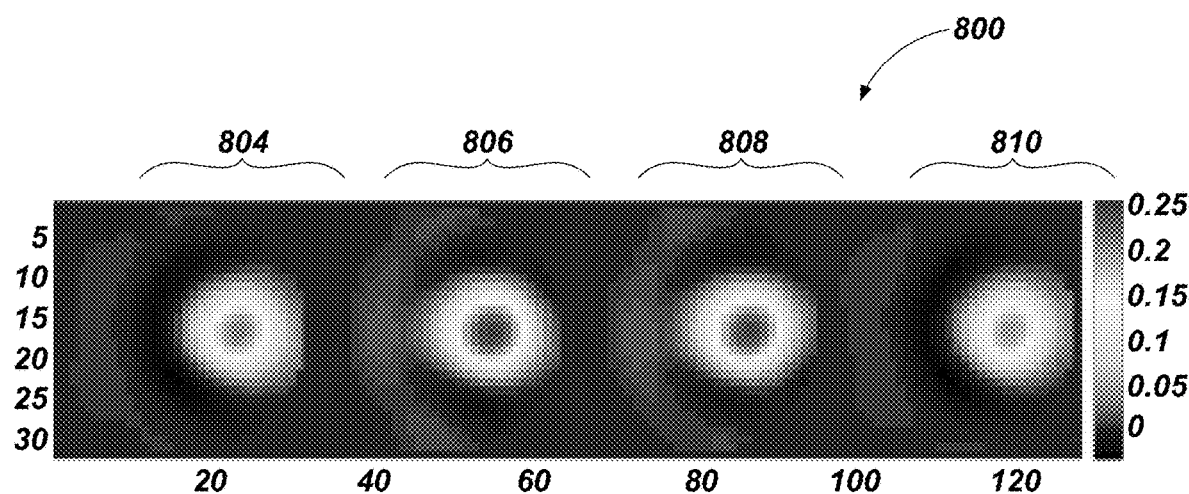
FIG. 8 is a reconstructed image corresponding to the finite element mesh of FIG. 7 according to an embodiment of the disclosure.

FIG. 8 is a set of reconstructed 2D images 800 corresponding to the finite element mesh 700 of FIG. 7 according to an embodiment of the disclosure. The reconstruction algorithm may be applied for each selected layer of the finite element mesh 700 (FIG. 7) to generate a corresponding 2D image. Generating a 2D image for a specific layer of the finite element mesh 700 (FIG. 7) may also be referred to as "focusing" on a specific layer to generate the 2D image in an isolated region. As shown in FIG. 8, an image 804 may be generated for layer 704, an image 806 may be generated for layer 706, an image 808 may be generated for layer 708, an image 810 may be generated for layer 710. The outermost layers 702, 712 are ignored in this example; however, corresponding images also could be generated if desired.

Thus, not only may images 806, 808 be generated for the electrode layers 706, 708 of the electrode planes, images 804, 810 corresponding to the electrode layers 704, 710 outside of the electrode planes may also be generated. As a result, the operator may have a real-time view of various phenomena occurring in the body in the regions outside of the electrode planes. Although the images for these regions may be lower resolution than if another plane of electrodes were included to align with that layer of the finite element mesh, obtaining such information without such a plane of electrodes may be desirable for cost considerations and/or for locations in which electrode placement may be undesirable or not even possible.

The different images may be combined for display to the operator as a single image as shown in FIG. 8. In some embodiments, the EIT system may perform the reconstruction for each selected layer at least substantially simultaneously (e.g., parallel processing of the reconstruction for each layer using its' respective reconstruction matrix). In some embodiments, however, a graphical user interface may enable the operator to select one or more of the images to be displayed while the others are hidden to be less distracting. In such embodiments, certain processing features may not be performed simultaneously or at all depending on the selection by the operator. For example, the operator may select fewer layers for display than are available. As a result, the EIT system may only perform the reconstruction processes for the selected layer(s) and not for the unselected layer(s). Thus, reconstruction images may be generated for the electrode layers or the regions outside the plane, either individually or in any combination. Of course, in some embodiments the EIT system may perform the reconstruction processes for layers that are not selected for display. Doing so may add computational complexity that may affect the image refresh rate. However, performing reconstruction processes for layers not selected for display may be useful if such images (or other data derived therefrom) is desired to be stored to be reviewed later or other patient record keeping requirements.

Such a graphical user interface may also be configured to select the finite element mesh to be used for a specific patient, as well as redefine the layers or other regions of interest for generating the images if the operator is not satisfied with the predefined regions for the finite element mesh. As a result of redefining new regions of interest ad hoc by the operator through the user interface, the EIT system may be configured to automatically generate new reconstruction matrices from the selected finite element mesh for use in a subsequent measurement and reconstruction cycle. Redefining the regions of interest of the finite element mesh may be implemented for a single use or saved and added to the library of finite element meshes for subsequent use if so desired by the operator.

Figure 9:
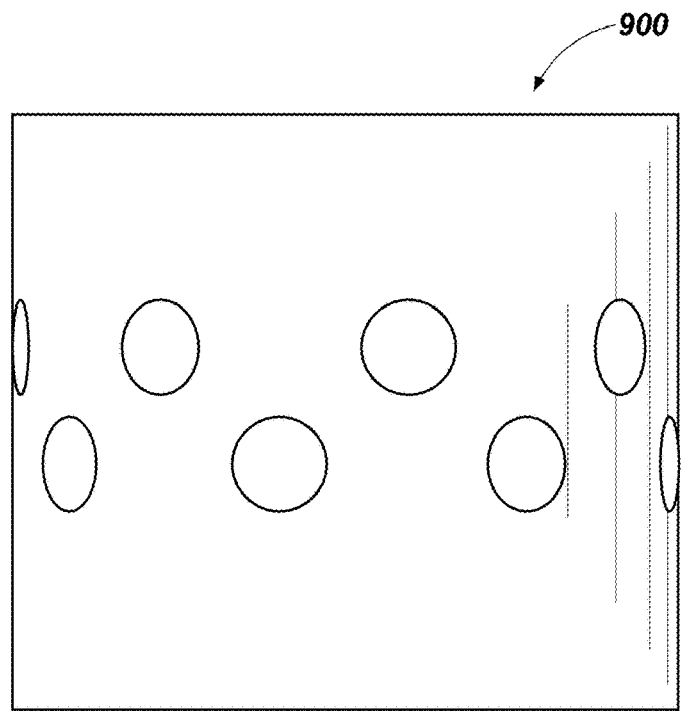
FIG. 9 is a side view of a schematic representation of a finite element mesh according to another embodiment of the disclosure.

FIG. 9 is a side view of a schematic representation of a finite element mesh 900 according to another embodiment of the disclosure. In contrast with the finite element mesh 700 of FIG. 7, the finite element mesh 900 may have regions of interest that are not defined as layers. In other words, the regions of interest may be non-linear (i.e., not a layer of uniform thickness) "irregular" or "arbitrary" (i.e., any desired shape or location). Such regions may be pre-defined and stored in the EIT device prior to use by the operator, or created by the operator during use. Reconstruction matrices may also be created for each region of interest for use by the EIT device when reconstructing the images. Thus, the mesh may include any number of regions of interest having any shape or location encompassing regions outside of the electrode layers, and a corresponding reconstruction matrix may be generated accordingly. The greater number of defined regions of interest and corresponding reconstruction matrices, the more accurate the reconstruction images may be by achieving higher granularity. More defined regions may have the tradeoff of memory and processing costs and reconstruction time; however, the inventors have appreciated that the higher granularity may be useful to reduce errors during the intermediate steps that generate the reconstruction matrices. Thus, whereas a uniform layer is clearly defined in the mesh of FIG. 7, in the mesh of FIG. 9 the layer is built when the mesh, parameters and regularization parameters are combined to generate the image reconstruction matrices.

Figure 10:
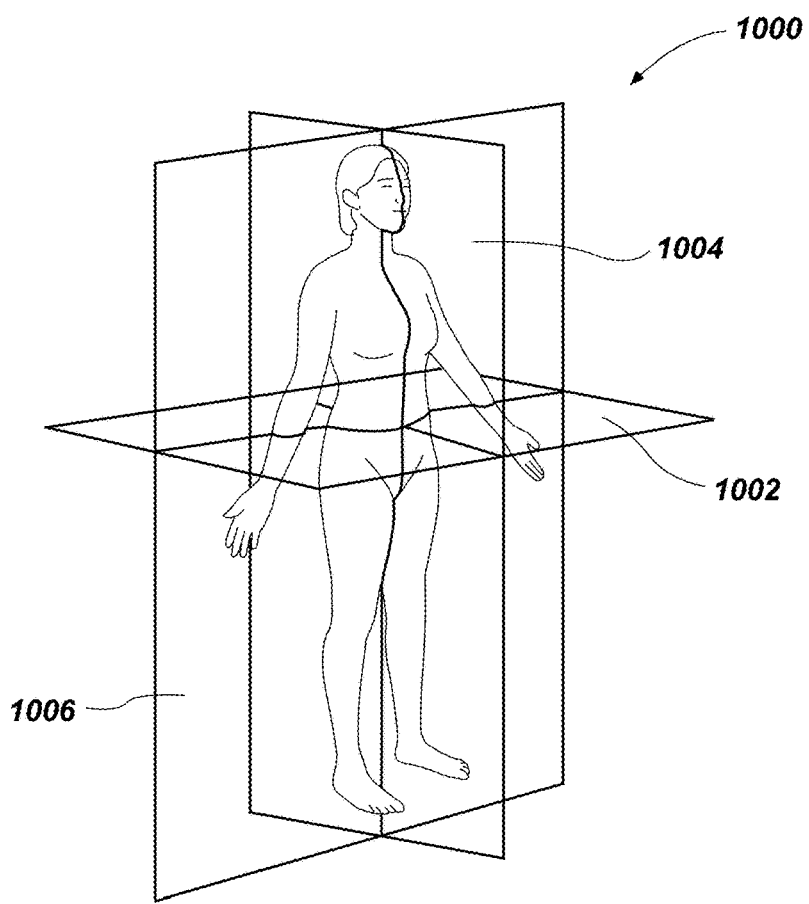
FIG. 10 is a representation of various planes of a body including a transverse plane, a sagittal plane, and a coronal plane.

FIG. 10 is a representation of various planes 1000 of a body including a transverse plane 1002, a sagittal plane 1004, and a coronal plane 1006. According to various embodiments, images reconstructed for the multi-planar EIT device along with the methods for generating images for regions outside of the electrode plane may provide images and other information for multiple transverse planes rather than just a single transverse plane. In addition, the same measurement data may be used to provide images and other information for the coronal plane and/or the sagittal plane as well.

Figure 11:
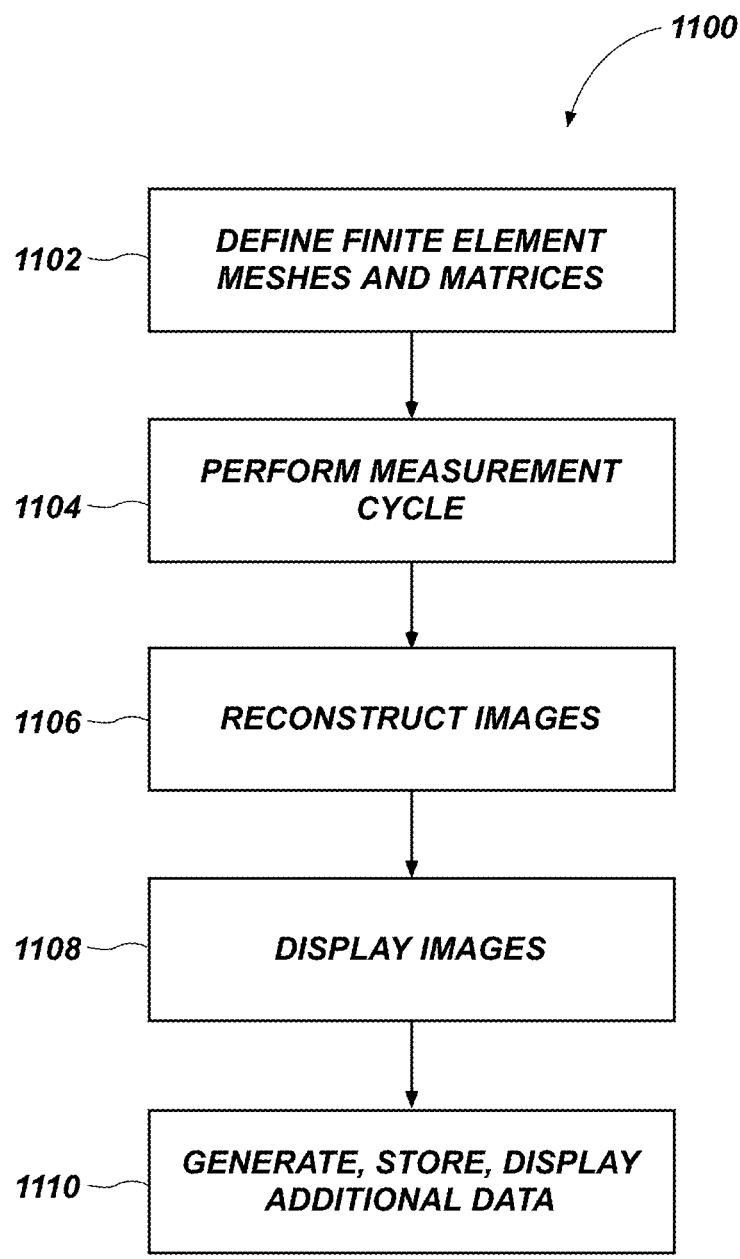
FIG. 11 is a flowchart illustrating a method of reconstructing an image using an electrical impedance tomography device according to an embodiment of the disclosure.

FIG. 11 is a flowchart 1100 illustrating a method of operating an electrical impedance tomography device according to an embodiment of the disclosure. At operation 1102, finite element meshes may be defined for different body shapes and body types. The finite element meshes may be stored in the memory device of the electrical impedance tomography device. Each finite element mesh may also have multiple regions of interest (e.g., random regions, defined layers, etc.) corresponding to the electrode layers of the electrode planes as well as regions of interest outside of the electrode planes. Each region of interest may have its own corresponding reconstruction matrix based on the finite element mesh to be used for reconstructing the image. The distribution of the resistivity may depend, at least in part on settings such as the selected mesh, the current pattern applied, and other reference values defined by the system as well as normalization equations. In addition, certain regularization parameters such as filters, sensitivity factors, and other parameters for the specific region of interest may also be utilized as would be understood by those of ordinary skill in the art. The operator may select the desired finite element mesh and the desired regions of interest for the specific patient prior to beginning the measurement cycle.

At operation 1104, a measurement cycle may be performed through the electrodes of the electrode belt positioned on a patient. The electrodes may be arranged in multiple horizontal planes as discussed above. A measurement cycle includes injecting excitation currents into successive pairs of electrodes while also performing voltage measurements by the other electrodes. Various current patterns and measurement patterns are contemplated as discussed above.

At operation 1106, images may be reconstructed from the voltage measurements and the selected finite element mesh. The image reconstruction may be performed for at least some of the different regions of interest defined for the finite element mesh by applying the measurements to the corresponding reconstruction matrix, including for at least one region located outside of the electrode regions and, if selected, for the electrode regions as well.

At operation 1108, the images may be displayed by the electronic display of the electrical impedance tomography device. As a result, multiple 2D images may be generated and displayed by the electrical impedance tomography device including in the plane of the electrodes as well as outside of the plane of the electrodes—giving the operator more real-time imaging information as to the phenomena occurring in the body than may be available by conventional systems.

At operation 1110, additional data may be generated, stored, and/or displayed by the EIT device. For example, additional data may include post processing data or other data (e.g., numeric data, graphs, trend information, and other information deemed useful for the operator). Such data may be derived from the voltage measurements and/or the reconstructed images.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the disclosure as hereinafter claimed, including legal equivalents thereof. In addition, features from one embodiment may be combined with features of another embodiment while still being encompassed within the scope of the disclosure. Further, embodiments of the disclosure have utility with different and various detector types and configurations.

What is claimed is:

1. An electrical impedance tomography system, comprising:
   an electrode belt comprising:
     a first set of electrodes, each electrode of the first set of electrodes intersecting a first horizontal plane when fitted to a subject; and
     a second set of electrodes, each electrode of the second set of electrodes intersecting a second different horizontal plane when fitted to the subject, wherein the first horizontal plane is spaced vertically from the second different horizontal plane when the electrode belt is fitted to the subject; and
   a data acquisition system operably coupled with the electrode belt, the data acquisition system comprising:
     at least one processor or programmable logic; and
     at least one non-transitory computer readable storage medium storing instructions thereon that, when executed by the at least one processor or programmable logic, cause the electrical impedance tomography system to:
       inject a first excitation current into a first pair of electrodes within the first set of electrodes of the electrode belt and within the first horizontal plane;
       subsequent to injecting the first excitation current into the first pair of electrodes, inject a second excitation current into a second pair of electrodes within the second set of electrodes of the electrode belt and within the second horizontal plane;
       receive voltage measurements from at least some of the electrodes of the first and second set of electrodes of the electrode belt;
       receive a selection of at least one region of a plurality of regions defined by a finite element mesh;
       reconstruct images from the received voltage measurements and for the selected at least one region of the finite element mesh via generated reconstruction matrices, the selected at least one region of the plurality of regions having a respective reconstruction layer;
       responsive to a user interaction, redefine boundaries of the at least one region of the plurality of regions to generate at least one new region; and
       reconstruct images from the received voltage measurements for the at least one new region of the finite element mesh.

2. The electrical impedance tomography system of claim 1, wherein the electrodes of the first set of electrodes are unaligned with the electrodes of the second set of electrodes in an axial direction.

3. The electrical impedance tomography system of claim 1, wherein the electrodes of the first set of electrodes are aligned with the electrodes of the second set of electrodes in an axial direction.

4. The electrical impedance tomography system of claim 1, wherein electrodes of the electrode belt are arranged in only the first set of electrodes and the second set of electrodes, which intersect the first and second horizontal planes, respectively.

5. The electrical impedance tomography system of claim 1, further comprising at least one third set of electrodes, each electrode of the third set of electrodes intersecting a third different horizontal plane when fitted to the subject.

6. The electrical impedance tomography system of claim 1, wherein the data acquisition system further comprises instructions, that when executed by the at least one processor or programmable logic, cause the electrical impedance tomography system to inject the excitation current according to a pattern by utilizing electrode pairs located within a same horizontal plane.

7. The electrical impedance tomography system of claim 6, wherein the each of the electrode pairs located within the same horizontal plane comprises two nonadjacent electrodes, and wherein at least one intermediate electrode is disposed between the two nonadjacent electrodes.

8. The electrical impedance tomography system of claim 6, wherein the data acquisition system further comprises instructions, that when executed by the at least one processor or programmable logic, cause the electrical impedance tomography system to inject the excitation current according to a pattern by utilizing electrode pairs located within the first horizontal plane before utilizing electrode pairs located within the second horizontal plane.

9. The system of claim 1, wherein injecting excitation currents into the first pair of electrodes within the first set of electrodes of the electrode belt and the second pair of electrodes within the second set of electrodes of the electrode belt comprises injecting the excitation currents by alternating between pairs of electrodes within the first set of electrodes of the electrode belt and pairs of electrodes within the second set of electrodes of the electrode belt.

10. The system of claim 1, further comprising instructions that, when executed by the at least one processor or programmable logic, cause the electrical impedance tomography system to:
    generate and display a graphical user interface displaying the reconstructed images for the at least one region of the plurality of regions;
    detect the user interaction with the graphical user interface to redefine the boundaries of the at least one region of the plurality of regions to generate at least one new region; and
    display the reconstructed images for the at least one new region within the graphical user interface.

11. The system of claim 1, further comprising instructions that, when executed by the at least one processor or programmable logic, cause the electrical impedance tomography system to:
    generate and display a graphical user interface for displaying reconstructed images; and responsive to receiving the selection of the at least one region, display the reconstructed image for the at least one region within the graphical user interface without displaying constructed images for any of the other regions of the plurality of regions.

12. An electrical impedance tomography system, comprising:
a data acquisition system comprising:
at least one processor or programmable logic; and
at least one non-transitory computer readable storage medium storing instructions thereon that, when executed by the at least one processor or programmable logic, cause the at least one processor or programmable logic to:
inject an excitation current into a first pair of electrodes within a first set of electrodes of an electrode belt and within a first horizontal plane;
subsequent to injecting the excitation current into the first pair of electrodes, inject a second excitation current into a second pair of electrodes within a second set of electrodes of the electrode belt and within a second different horizontal plane;
receive voltage measurements from at least some electrodes of the first and second set of electrodes of the electrode belt;
receive a selection of a subset of regions of a plurality of regions defined by a finite element mesh;
reconstruct images from the received voltage measurements and for the selected regions of the finite element mesh via generated reconstruction matrices, each region of the subset of regions having a respective reconstruction layer;
responsive to a user interaction, redefine boundaries of one or more regions of the subset of regions of the plurality of regions to generate one or more new regions; and
reconstruct images from the received voltage measurements for the one or more new regions of the finite element mesh.

13. The electrical impedance tomography system of claim 12, wherein the data acquisition system further includes instructions that, when executed by the at least one processor or programmable logic, cause the at least one processor or programmable logic to: reconstruct images for at least one region of interest outside of the first and second horizontal planes intersected by the first and second sets of electrodes.

14. The electrical impedance tomography system of claim 12, wherein the data acquisition system further includes instructions that, when executed by the at least one processor or programmable logic, cause the at least one processor or programmable logic to: reconstruct images for at least one non-uniform region of interest.

15. The electrical impedance tomography system of claim 12, wherein the data acquisition system further includes instructions that, when executed by the at least one processor or programmable logic, cause the at least one processor or programmable logic to: reconstruct images via the finite element mesh.

16. The electrical impedance tomography system of claim 12, wherein the data acquisition system further includes instructions that, when executed by the at least one processor or programmable logic, cause the at least one processor or programmable logic to: generate a graphical user interface configured to enable an operator to select the finite element mesh from among a library of finite element meshes stored in the at least one non-transitory computer readable storage medium utilized in reconstructing images.

17. The electrical impedance tomography system of claim 16, wherein the graphical user interface is further configured to enable the operator to select specific regions within the selected finite element mesh for generating and displaying the corresponding reconstructed images using corresponding reconstruction matrices.

18. A method of operating an electrical impedance tomography device, the method comprising:
injecting an excitation current into successive pairs of electrodes in an electrode belt comprising:
a first set of electrodes, each electrode of the first set of electrodes intersecting a first horizontal plane when fitted to a subject; and
a second set of electrodes, each electrode of the second set of electrodes intersecting a second different horizontal plane when fitted to the subject,
wherein the first horizontal plane is spaced vertically from the second different horizontal plane when the electrode belt is fitted to the subject,
wherein each successive pair of electrodes comprises two nonadjacent electrodes, and wherein at least one intermediate electrode is disposed between the two nonadjacent electrodes, and
wherein a first pair of electrodes of the successive pairs of electrodes is within the first set of electrodes and within the first horizontal plane and a second immediately subsequent pair of electrodes of the successive pairs of electrodes is within the second set of electrodes and within the second horizontal plane;
measuring a voltage response utilizing at least some of the electrodes of the first and second sets of electrodes of the electrode belt;
receiving a selection of at least one region of a plurality of regions defined by a finite element mesh;
reconstructing images from the received voltage measurements and for the selected at least one region of the finite element mesh via generated reconstruction matrices, the selected at least one region of the plurality of regions having a respective reconstruction layer;
responsive to a user interaction, redefining boundaries of the at least one region of the plurality of regions to generate at least one new region; and
reconstructing images from the received voltage measurements for the at least one new region of the finite element mesh.

19. The method of claim 18, wherein reconstructing the images includes applying the measured voltages to reconstruction matrices generated from a selected finite element mesh having multiple defined layers corresponding to the first and second horizontal planes intersecting the electrodes of the first and second sets of electrodes and for at least one region outside of the first and second horizontal planes of intersecting the electrodes of the first and second sets of electrodes.

20. The method of claim 19, wherein the multiple defined layers for the selected finite element mesh are predetermined and stored in a memory device of the electrical impedance tomography device for selection from among a library of predetermined finite element meshes.

* * * * *